(12) United States Patent
Stoicescu et al.

(10) Patent No.: US 9,680,412 B2
(45) Date of Patent: Jun. 13, 2017

(54) METHOD AND APPARATUS FOR TESTING PHOTOVOLTAIC MODULES

(71) Applicant: Solarzentrum Stuttgart GmbH, Stuttgart (DE)

(72) Inventors: Liviu-Mihai Stoicescu, Stuttgart (DE); Michael Reuter, Stuttgart (DE); Juergen H. Werner, Stuttgart (DE)

(73) Assignee: SOLARZENTRUM STUTTGART GMBH, Stuttgart (DE)

(*) Notice: Subject to any disclaimer, the term of this patent is extended or adjusted under 35 U.S.C. 154(b) by 169 days.

(21) Appl. No.: 14/615,461

(22) Filed: Feb. 6, 2015

(65) Prior Publication Data

US 2015/0155829 A1    Jun. 4, 2015

Related U.S. Application Data

(63) Continuation of application No. PCT/EP2013/066701, filed on Aug. 9, 2013.

(30) Foreign Application Priority Data

Aug. 9, 2012    (DE) .................. 10 2012 107 316

(51) Int. Cl.
*H02S 50/15* (2014.01)
*G01N 21/66* (2006.01)
*H02S 50/10* (2014.01)

(52) U.S. Cl.
CPC ............. *H02S 50/15* (2014.12); *G01N 21/66* (2013.01); *H02S 50/10* (2014.12)

(58) Field of Classification Search
CPC combination set(s) only.
See application file for complete search history.

(56) References Cited

U.S. PATENT DOCUMENTS

2009/0102453 A1\* 4/2009 Kasahara ........... G01N 21/8806
324/96
2009/0297017 A1 12/2009 Hudgings et al.
(Continued)

FOREIGN PATENT DOCUMENTS

AU    WO 2010019992 A1 \*    2/2010 ......... G01N 21/6489
CN    101960579 A    1/2011
(Continued)

OTHER PUBLICATIONS

Coello, Jorge; Introducing Electroluminescence Technique in the Quality Control of Large PV Plants; 26th European Photovoltaic Solar Energy Conference and Exhibition; 2011; pp. 3469-3472.
(Continued)

*Primary Examiner* — Clayton E Laballe
*Assistant Examiner* — Jas Sanghera
(74) *Attorney, Agent, or Firm* — Harness, Dickey & Pierce, P.L.C.

(57) ABSTRACT

A method and an apparatus for testing photovoltaic modules are provided, wherein power that a photovoltaic module outputs or draws is modulated a modulating frequency, the photovoltaic module is scanned using a camera and the camera signal generated by the camera is evaluated in order to obtain a luminescence image of the photovoltaic module which is used for detecting defects on the photovoltaic module. The photovoltaic module is operated only in the forward direction and the camera signal is evaluated using a digital filter, such as a lock-in filter.

20 Claims, 5 Drawing Sheets

(56) References Cited

U.S. PATENT DOCUMENTS

| | | |
|---|---|---|
| 2010/0073665 A1 | 3/2010 | Zhao et al. |
| 2010/0074515 A1 | 3/2010 | Zhao et al. |
| 2010/0201374 A1 | 8/2010 | Vasilyev et al. |
| 2012/0032687 A1 | 2/2012 | Kyomasu et al. |
| 2012/0126120 A1 | 5/2012 | Fuyuki et al. |
| 2012/0160295 A1 | 6/2012 | Clevenger et al. |

FOREIGN PATENT DOCUMENTS

| | | |
|---|---|---|
| CN | 102365558 A | 2/2012 |
| CN | 102472791 A | 5/2012 |
| CN | 102629968 A | 8/2012 |
| DE | 44 40 167 A1 | 8/1996 |
| DE | 102 40 060 A1 | 3/2004 |
| DE | 10 2007 010 516 A1 | 9/2008 |
| DE | 10 2010 010 509 A1 | 9/2011 |
| EP | 2 410 319 A1 | 1/2012 |
| EP | 2 421 052 A2 | 2/2012 |
| EP | 2 463 672 A1 | 6/2012 |
| JP | 2010-181328 | 8/2010 |
| WO | 2008/095467 A1 | 8/2008 |

OTHER PUBLICATIONS

O. Breitenstein et al.; Lock-in Thermography—Basics and Use for Evaluating Electronic Devices and Materials; 2010; pp. 14-22.
Morgan D. Bazilian et al.; Thermographic analysis of a building integrated photovoltaic system; 2002; pp. 449-461.
International Search Report; Nov. 8, 2013; 14 pp.
Liviu Stoicescu et al.; "Daylight Luminescence for Photovoltaic System Testing;" Nov. 2012; 3 pp.
Liviu Stoicescu; "DaySy Daylight Luminescence System;" Jul. 4, 2013; 16 pp.

\* cited by examiner

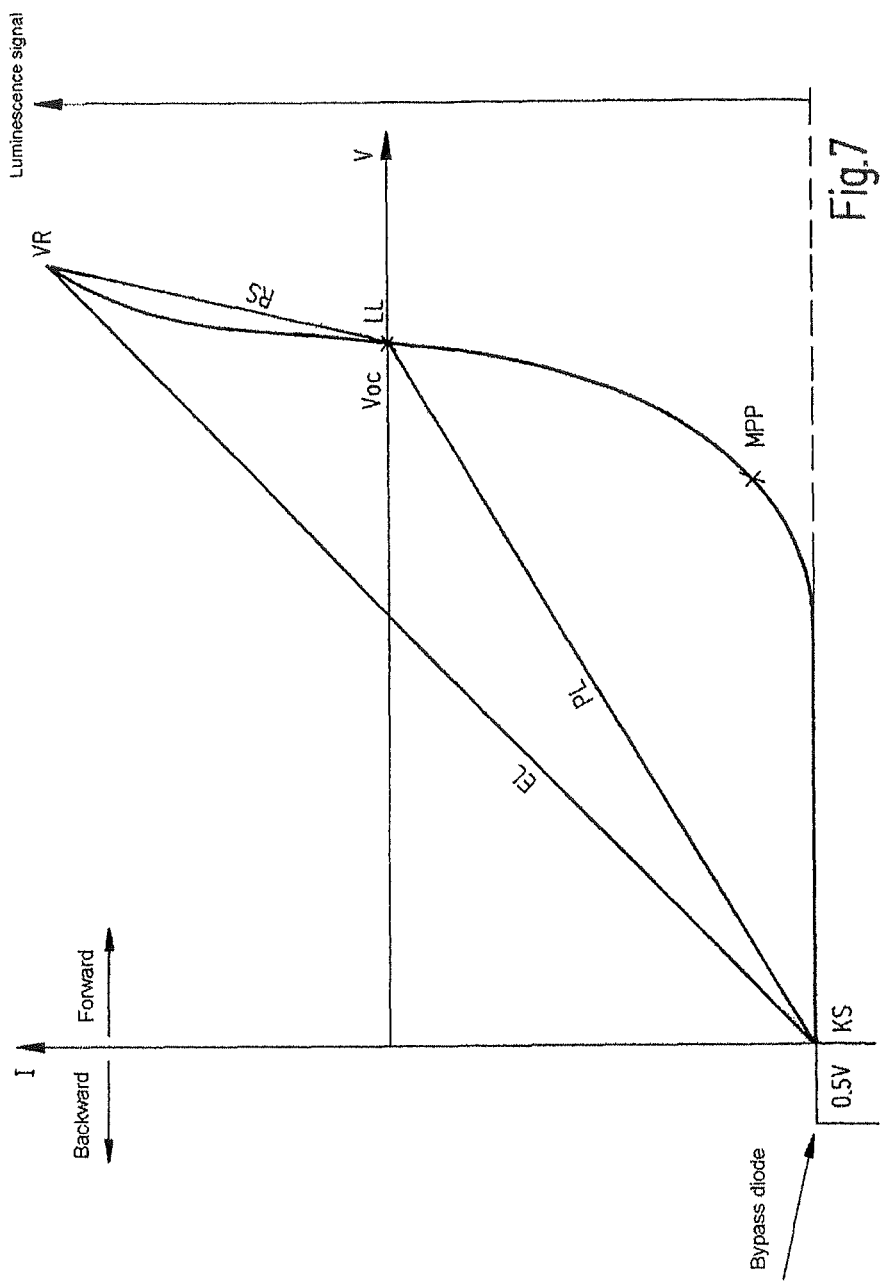

METHOD AND APPARATUS FOR TESTING PHOTOVOLTAIC MODULES

CROSS-REFERENCES TO RELATED APPLICATIONS

This application is a continuation of international patent application PCT/EP2013/066701, filed on Aug. 9, 2013 designating the U.S., which international patent application has been published in German language and claims priority from German patent application DE 10 2012 107 316.3, filed on Aug. 9, 2012. The entire contents of these priority applications are incorporated herein by reference.

BACKGROUND OF THE INVENTION

The invention relates to a method for testing photovoltaic modules, comprising the following steps:
an AC voltage is modulated onto a photovoltaic module;
the photovoltaic module is scanned using a camera; and
the camera signal produced by the camera is evaluated in order to obtain a luminescence image of the photovoltaic module.

The invention additionally relates to an apparatus for testing a photovoltaic module, having a device for modulating an AC voltage signal onto the photovoltaic module, having a camera for scanning the photovoltaic module, which camera outputs a camera signal, and having an evaluation device for computing a luminescence image from the camera signal.

Such a method and such an apparatus are known from EP 2 421 052 A2.

According to the known method and the known apparatus, an AC voltage signal is applied to both connections of the photovoltaic module and the modulation is performed both in the forward direction and in the backward direction of the photovoltaic module and the resultant electroluminescence is evaluated. This prompts luminescence images to be captured in the forward direction and in the backward direction and superimposed on one another.

The known method is used for quality control during the manufacture of photovoltaic modules. Like all currently known methods that are based on luminescence, it needs to be performed in a dark room with the exclusion of any sources of illumination, apart from the photovoltaic module itself. In addition, it cannot be used for photovoltaic modules having integral bypass diodes.

J. Coello, "Introducing Electroluminescence Technique as a Quality Control of Large PV Plants" in "26th European Photovoltaic Solar Energy Conference and Exhibition", pages 3469-3472, 2011, discloses quality control during the manufacture of photovoltaic modules on a large scale by electroluminescence. In this case, the photovoltaic cells have a DC voltage applied to them in the forward direction, so that they radiate in the near infrared range. In this case too, the test is performed in a dark room, without the presence of daylight.

Although such test methods are fundamentally suited to ensuring good quality control during the manufacture of photovoltaic cells, use on already existing photovoltaic modules requires the module in question to be demounted and checked in the dark room.

This means a very high level of outlay and leads to corresponding losses during the checking phase.

SUMMARY OF THE INVENTION

In view of this it is a first object of the invention to disclose a method and an apparatus for testing photovoltaic modules that allow for a simplified test suitable for application without a dark room.

It is a second object of the invention to disclose a method and an apparatus for testing photovoltaic modules that allow for testing while the photovoltaic modules are in operation.

It is a third object of the invention to disclose a method and an apparatus for testing photovoltaic modules that allow for detecting various defects on the photovoltaic modules in a simple and reliable way.

It is a forth object of the invention to disclose a method and an apparatus for testing photovoltaic modules that can be used on existing photovoltaic module systems in a simple and reliable way.

These and other objects are achieved according to one aspect by a method for testing photovoltaic modules, comprising the following steps:
modulating a power drawn from or output by a photovoltaic module using at least one modulation frequency, while operating said photovoltaic module in a forward direction thereof;
scanning said photovoltaic module using a camera for outputting a camera signal; and
evaluating said camera signal using an algorithm for generating from said camera signal a luminescence image of said photovoltaic module.

According to one further aspect these and other objects are achieved by an apparatus for testing a photovoltaic module while being operated in forward direction, said apparatus comprising:
a modulator for modulating an AC voltage signal onto the power drawn or output by said photovoltaic module using at least one modulation frequency;
a camera arranged for scanning said photovoltaic module, said camera outputting a camera signal;
an evaluation device for evaluating said camera signal using an algorithm for computing a luminescence image from said camera signal.

According to the invention, selective evaluation of the electroluminescence and isolation of sources of interference that are existent during the operation of the photovoltaic module, such as reflections from the sun or from the surroundings, are made possible using the filter while the power of the module is being modulated.

In the course of this application, "forward direction" is understood to mean that voltage range in which the voltage that is present on the module has the same polarity as the voltage drop across the module under illumination at no load.

In a preferred development of the invention, the camera has a filter system connected upstream of it that is transmissive in the wavelength range that contains the luminescence signals from the photovoltaic module, for example is transmissive to photovoltaic modules made of crystalline silicon, particularly in the near infrared range (NIR), to which end it is possible to use an optical filter, for example. This results in optimum sensitivity in the wavelength range of the electroluminescence and in good isolation from the remainder of the interference signals.

According to the invention, the photovoltaic module can even be tested in daylight or other irradiation, preferably even during operation of the photovoltaic module.

In a preferred embodiment of the invention, the camera signal is evaluated by means of a digital filter.

In the course of this application, a "digital filter" is understood to mean a mathematical filter for manipulating a signal, such as rejecting or passing a particular frequency range. Digital filters do not process continuous signals but rather process exclusively discrete-time and discrete-value signals. A discrete-time signal consists only of individual pulses (in this case: images) that represent the signal profile over time, the respective samples (in this case: the brightness values of the image points), in a temporally periodic sequence. The samples are in discrete-value form, since the digital numerical representation provides only a finite resolution.

A digital filter can be used to extract and evaluate the luminescence image cleanly despite heavy background noise, as occurs on a photovoltaic module in daylight, for example.

If a digital filter is used, the additional upstream connection of an (optical) filter system before the camera makes sense only if there is no wideband interference present at the same time as a wideband useful signal. However, if (a) there is wideband interference and a narrowband useful signal (e.g. daylight luminescence) present then, given the correct choice of filter, the signal-to-noise ratio (SNR) can be increased by a factor of 10 to 100. If, in case (b), the spectral ranges of the interference signal and the useful signal are totally different (e.g. photoluminescence in a dark room), it is even possible for the SNR to be increased by a factor of $10^6$ or more.

Since case (a) obtains as a rule, the upstream connection of an optical filter system before the camera additionally makes sense for using a digital filter.

According to a further preferred embodiment of the invention, the camera signal is evaluated using the lock-in method.

The lock-in method is fundamentally known in the prior art and is frequently used when signals need to be amplified and, against the background of static noise, evaluated. As described in detail in O. Breitenstein, W. Warta and M. Langenkamp, Lock-in Thermography. Basics and Use for Evaluating Electronic Devices and Materials, online issue (Springer-Verlag Berlin Heidelberg, Berlin, Heidelberg, 2010), which is included in full here by way of reference, the lock-in method requires the primary signal to be amplitude-modulated using a particular frequency, the "lock-in frequency", in periodically pulsed fashion or in any way prior to the detection and prior to the first gain stage.

The aim of the lock-in method is to evaluate only the oscillating AC voltage portion of the detected signal. In the case of the analogue variant of the lock-in method, a noise-free AC reference signal is derived from the signal generation process and, as a phase-shifting signal, alternately either directly superimposed with the noisy measurement signal using an electronic switch or superimposed with the inverted noisy signal. In this way, the signal can be extracted largely noise-free. It goes without saying that instead of the aforementioned analogue lock-in method it is also possible for the lock-in method to be realized in digital form, as explained in detail in O. Breitenstein et al., see above. Preferably, the lock-in method is thus likewise a digital filter method.

According to a further embodiment of the invention, the photovoltaic module has a modulation frequency ($f_Q$) impressed onto it that is used to change periodically between at least two operating points (KS, LL, MPP, VR).

In this case, the operating points used may be at least two that are selected from the group that consists of short circuit (KS), no load (LL), maximum power point (MPP) or any point in the forward direction (VR).

In a preferred development of the invention, information is extracted from the luminescence signals at different operating points (KS, LL, MPP, VR) by difference formation.

The luminescence signals in the case of the various operating points contain different information in respect of the luminescence, which information is evaluated according to the invention. In this connection, the short-circuit luminescence (KL), photoluminescence (PL), limited-resistance electroluminescence (EL) and background (H) are of interest, for example.

It is thus possible for the photoluminescence (PL) to be extracted by subtracting the luminescence signals at no load (LL) and under short circuit (KS), for example: LL−KS=PL.

This results in the no-load voltage of the solar cells incorporated in the photovoltaic module. It is also possible for uncontacted (dead) regions, microfissure and potential-induced degradation (PID) to be established.

In addition, the limited-resistance electroluminescence (EL) can be extracted by subtracting the luminescence signals in the forward direction (VR) and at no load (LL): EL=VR−LL.

This provides information regarding the local series resistance. It is a simple matter to identify regions that have poor electrical connection (interrupted fingers, poor solder joints and broken cell connectors), and also a microfissure and potential-induced degradation (PID).

In addition, a mixed luminescence signal (EL+PL) can be extracted by subtracting the luminescence signals in the forward direction (VR) and in the short circuit (KS): EL+PL=VR−KS.

This provides advice about the general quality of the photovoltaic module, particularly about microfissures and potential-induced degradation. The advantage of a high SNR can be exploited.

The camera video frequency (frame rate) $f_K$ is not stipulated, but rather is limited by today's technology. At present, the maximum is 400 Hz; a rapid rise can be expected in the next few years, however.

Conventionally, "oversampling" is used for signal amplification by means of lock-in. In this case, $f_Q \leq f_K/2$ is valid for the modulation frequency $f_Q$ in the case of single-phase lock-in and $f_Q \leq f_K/4$ is valid in the case of dual-phase lock-in. This is what is known as the Nyquist condition. However, it is also possible to use "under-sampling". In this case, $f_Q$ is independent of $f_K$. $f_Q$ may even be greater than $f_K$. In this case, however, there are some special features to be noted, such as "forbidden" frequencies (c.f. also O. Breitenstein et al., loc. cit.). The modulation frequency $f_Q$ does not have to be fixed. If the modulation signal is known, e.g. through extraction from the sum of all pixels in the image, asynchronous lock-in can be used to amplify the desired signal nevertheless.

If the lock-in method is used in conjunction with the method according to the invention, just a very weak electroluminescence signal can be cleanly isolated from heavy background noise, as occurs on a photovoltaic module in daylight, and evaluated in order to produce a luminescence image of the photovoltaic module.

It goes without saying that instead of the lock-in method it is also possible to use any other digital or analogue filter method that is suited to detecting weak periodic signals.

On the basis of the lock-in thermography method known from O. Breitenstein et al., a solar cell is modulated using the lock-in reference frequency via an external voltage source or radiation source. For the purpose of evaluation, an infrared camera that is sensitive in the mid-infrared range at wavelengths between 2 μm and 5 μm is used. The modulated voltage source or radiation source and the infrared camera are extremely precisely in sync with one another in this case in order to use the lock-in method to produce thermal images from the noisy frames, which thermal images indicate the precise position and severity of defects in the solar cell.

By contrast, the invention prompts the use of the lock-in method, or of another method that allows weak periodic signals to be detected, in order to evaluate or produce luminescence images from noisy images in the dark, in the presence of daylight or in other irradiation. Consequently, the thermography method known in the prior art from O. Breitenstein et al. is not suited to render the subject matter of the invention obvious, since according to the invention a luminescence image is generated by contrast to the thermal image generated in the prior art.

The periodic signal can be produced either optically (by additive or subtractive (supplementary) irradiation), mechanically (e.g. by shaking the module or by chopper), electrically or thermally (periodic cooling or heating) or magnetically.

According to a more advantageous embodiment of the invention, the test is performed with a load connected, preferably using an inverter.

This embodiment can be used particularly advantageously in practice, since the photovoltaic module to be tested does not need to be demounted but rather can be tested during operation, if need be utilizing the inverter itself.

According to a more advantageous embodiment of the invention, the modulation frequency $f_Q$ is produced by periodic switching on/off, preferably by means of a semiconductor switch.

This is a particularly simple way of producing the modulation frequency $f_Q$.

In this case, the frequency of the inverter can be used for the MPP search (Maximum Power Point Search) if need be.

According to a further embodiment of the invention, the inverter is actuated via an interface in order to modulate the connected modules using the modulation frequency $f_Q$.

Since more recent inverters are usually equipped with an interface for actuation, this allows the production of particularly simple modulation of the AC voltage signal onto the photovoltaic module or onto a succession of photovoltaic modules in a phase of an inverter.

According to a further embodiment of the invention, the photovoltaic module is preferably periodically shorted via a semiconductor switch.

This method also allows simple production of the modulation frequency.

According to a further embodiment of the invention, the photovoltaic module to be tested is modulated by periodic modulation of the irradiation on the same module or on a module connected in the same phase or to the same inverter, or on portions of said module, using the modulation frequency $f_Q$.

By way of example, this method can be implemented by specific periodic shading, for example by means of a chopper, using the modulation frequency $f_Q$.

Within the context of this application, irradiation covers any type of electromagnetic radiation: from X-radiation through UV, visible light, near, mid, far infrared into the microwave range.

When a camera with a 50-Hz frame frequency was used, good results were obtained using a modulation frequency in the range from approximately 1 to <25 Hz, for example in the range from 2 to 10 Hz or preferably in the range from 3 to 7 Hz.

The filter system filters the relatively weak electroluminescence signal, which (in the case of photovoltaic modules made of crystalline silicon) is in the near infrared range, namely in the range from 950 to 1330 nm, for example, with a maximum at 1130 nm, out of the background noise and thus allows better subsequent amplification using the lock-in method. Commonly used CCD cameras have relatively low sensitivity in the NIR range and greater sensitivity in the visible range.

These disadvantages are compensated for by the use, in addition to the filtering, of a camera that is matched to the luminescence spectrum of the module, said camera having high sensitivity in the wavelength range from 950 to 1350 nm for modules made of crystalline silicon, for example.

Cadmium telluride (CdTe) thin-layer modules emit light in the range from 700-900 nm. This is suited to the use of an SiCCD camera with a matched optical filter system.

CIGS (also CIGSSe or CIS) thin-layer modules emit light in a range between 800 1300 nm, depending on layer structure. This is suited to the use of an SiCCD camera with a matched optical filter system.

For all module technologies existing on the market, an InGaAs camera with a spectral range extended toward lower wavelengths (400-1700 nm) is suitable. The optical filter system should be matched accordingly.

It goes without saying that the features cited above and those yet to be explained below can be used not only in the respectively indicated combination but also in other combinations or on their own without departing from the scope of the present invention.

BRIEF DESCRIPTION OF THE DRAWINGS

Further features and advantages of the invention will emerge from the description of preferred exemplary embodiments below with reference to the drawing, in which:

FIG. 7 shows a current/voltage characteristic for a photovoltaic module, for which characteristic the various operating points are explained.

DESCRIPTION OF PREFERRED EMBODIMENTS

Figure 1:
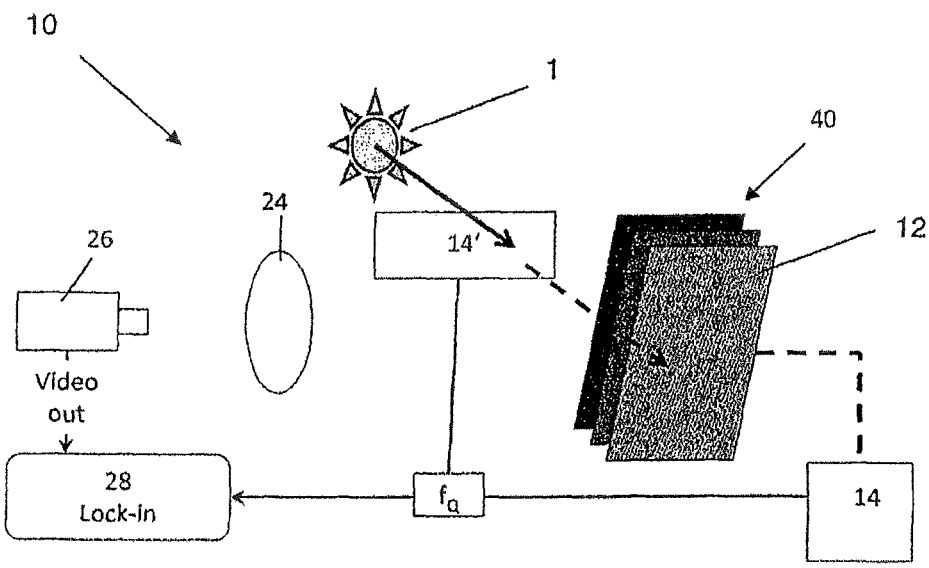
FIG. 1 shows a highly simplified overview of an apparatus according to the invention for testing a photovoltaic module.

FIG. 1 shows a simplified illustration of an apparatus 10 for testing a photovoltaic module 12 in a photovoltaic installation 40. The photovoltaic installation 40 has a succession of photovoltaic modules, which are indicated by 12 merely by way of example in this case.

The power of the photovoltaic installation 40 is modulated by means of at least one modulation frequency $f_Q$, as shown schematically using a source 14 or alternatively using a source 14'. By way of example, the modulation can be effected electrically, mechanically or magnetically in order to modulate the power that is output by the photovoltaic modules 12 using the modulation frequency $f_Q$ during operation, as shown at 14. Alternatively, by way of example, the radiation that is incident on the photovoltaic modules 12 could be modulated by the sun 1, for example by virtue of a chopper producing periodic shading, as shown at 14'.

The power that is output by the photovoltaic modules 12 and that is modulated using the modulation frequency $f_Q$ is scanned using a video camera 26. The output signal from the video camera 26 "video out" is analyzed by means of an evaluation device 28 (usually a PC) using a lock-in algorithm in order to derive luminescence images of the photovoltaic modules 12 therefrom.

Figure 2:
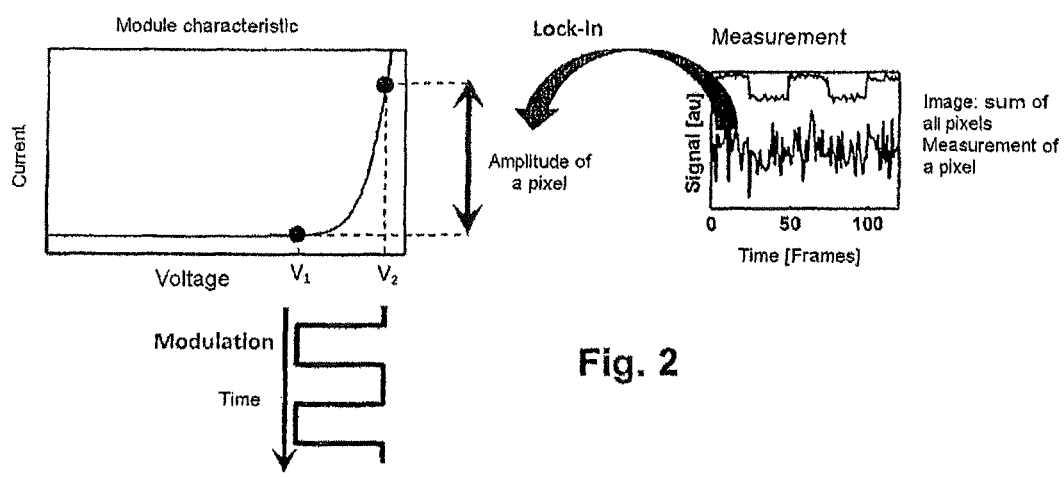
FIG. 2 shows a basic illustration of the modulation method for testing photovoltaic modules in a photovoltaic installation.
Figure 3:
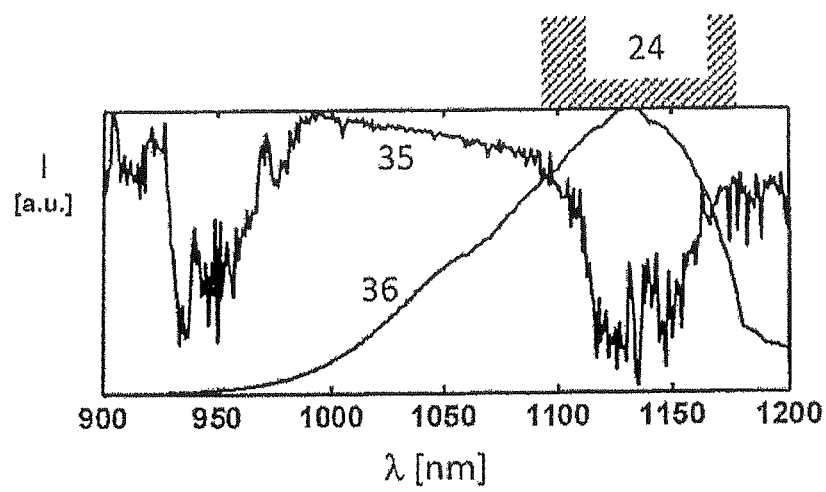
FIG. 3 shows a simplified schematic illustration of the spectral sensitivity of the filter system for the luminescence signal from solar modules made of crystalline silicon, which luminescence signal has a maximum in the region of approximately 1130 nm, and of the background noise in comparison therewith.

FIG. 2 schematically shows the modulation. By way of example, a module characteristic is modulated using a square-wave signal, as shown in the left-hand half of the image. The camera 26 is used to measure the individual pixels, as shown in the right-hand half of the image. From the sum of all pixels in the image, it is possible to determine the modulation frequency. From the noisy signal of each pixel, a luminescence image of the photovoltaic module is derived by means of the digital filter, in this case preferably in the form of the lock-in algorithm. FIG. 3 shows a schematic illustration of the background signal (intensity I in arbitrary units a.u.), which is denoted by 35, of the luminescence signal, which is denoted by 36, and of the filter system 24 used, which is predominantly sensitive in the range from 950 to 1350 nm, in order to put the sensitivity into the region of the maximum of the luminescence signal, which is 1130 nanometers for photovoltaic modules made of crystalline silicon. For other module technologies (e.g. thin-layer modules), the measuring system can be matched accordingly.

Figure 4:
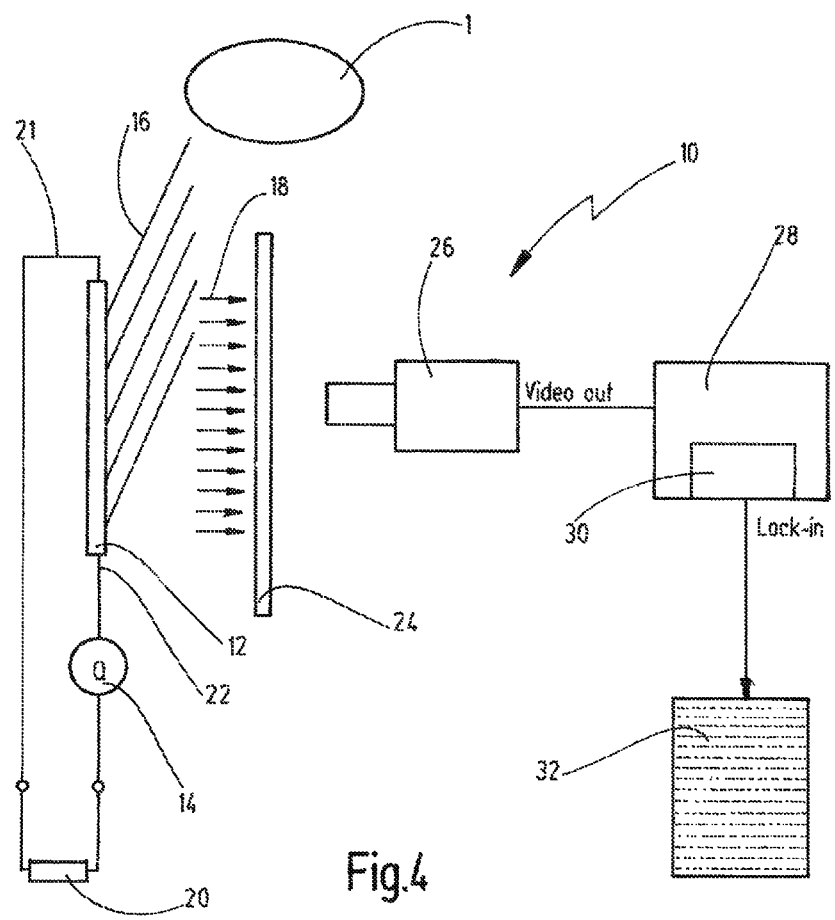
FIG. 4 shows a further basic illustration of an apparatus according to the invention, wherein the modulation frequency is produced by a source in the circuit of the photovoltaic module, as a result of which an AC voltage signal is impressed.

FIG. 4 shows a further illustration of an apparatus 10 for testing a photovoltaic module 12.

The photovoltaic module 12 has two connections 21, 22 that it uses to form a completed circuit when an external load 20 is connected. This circuit also contains another source 14 for producing a periodic signal that is superimposed.

According to the invention, the source 14 is used to produce a periodic AC voltage signal, the amplitude of which is chosen such that the photovoltaic module 12 is always operated in its forward direction. By way of example, said signal may be a sinusoidal signal, the amplitude of which is smaller than the amplitude of the DC signal that is produced by virtue of the photovoltaic module 12 being irradiated by means of sunbeams 16 from a schematically shown sun 1. The result would then be a pulsating signal, the amplitude of which pulsates between 11 and 12, as indicated schematically in FIG. 5.

The luminescence radiation 18 produced by the photovoltaic module 12 when operated in its forward direction is filtered out using the filter system 24, which operates in the range from 950 to 1350 nm with a maximum in the region of 1130 nm, for example, in order to extract the luminescence signal from the background noise of the solar spectrum 35 shown in FIG. 3. The camera 26 receives the signal filter using the filter system 24 and scans the surface of the photovoltaic module 12. By way of example, the frame frequency of the camera 26 may be 50 Hz ($f_K$=50 Hz). As modulation frequency $f_Q$, it would be possible to use a frequency of 5 Hz, for example.

The output signal "video out" from the camera 26 is supplied to the evaluation device 28, for example a PC, for evaluation. The evaluation device 28 uses a digital lock-in algorithm 30 in order to extract the electroluminescence signal from the noisy video signal and to amplify it and in order to produce a luminescence image 32 of the photovoltaic module 12 therefrom. The luminescence image 32 can then be used to render defects in the photovoltaic module 12 visible or to automatically evaluate such defects.

As has already been explained above, it goes without saying that the excitation signal can be produced in any way provided that care is taken to ensure that the photovoltaic module 12 is only ever operated in the forward direction. In addition, besides square-wave or sinusoidal excitation signals, any other periodic modulation signals are also conceivable.

Figure 5:
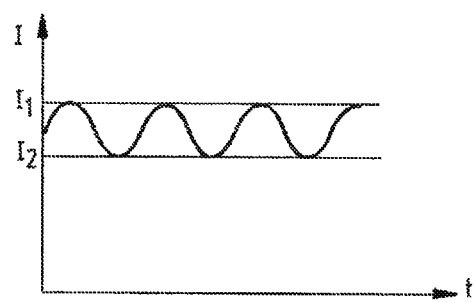
FIG. 5 shows an alternative embodiment of the invention in which the modulation frequency is in the form of a sinusoidal signal that is used to modulate the output power of a photovoltaic module, for example.

As already mentioned above, instead of a sinusoidal signal as shown in FIG. 5, a square-wave signal as shown in FIG. 2 could also be used, for example. By way of example, a square-wave signal of this kind can be produced in a simple manner by virtue of the circuit of the photovoltaic module 12, completed via the load 20, accommodating a switch that is used to periodically break or complete the circuit. In this case, the source 14 shown in FIG. 4 would be a semiconductor switch. Alternatively, it would also be possible for the photovoltaic module 12 to be periodically shorted via a semiconductor switch, for example.

Figure 6:
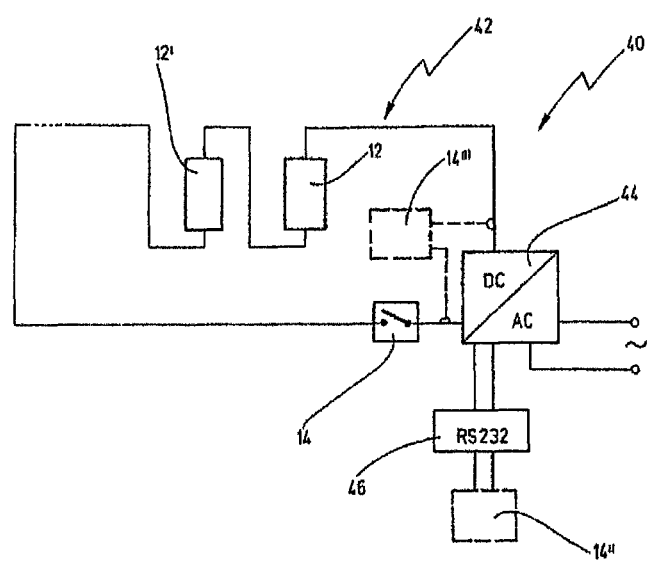
FIG. 6 shows a simplified illustration of a photovoltaic installation having a succession of series-connected photovoltaic modules in a phase of an inverter, with various options for producing the modulation frequency.

A few variants for production of the excitation signal in conjunction with an inverter are shown in FIG. 6 on the basis of an exemplary photovoltaic installation 40.

In the present case, an array of photovoltaic modules 12, 12' . . . are connected up in series and form a phase 42 that is connected to an inverter 44. It goes without saying that the photovoltaic installation 40 usually has a plurality of phases, which are not shown in the present case for reasons of simplicity, however.

In the present case, the phase 42 contains a semiconductor switch 14 in series with the photovoltaic modules 12, 12'. The semiconductor switch 14 can therefore periodically interrupt the phase current, so that the situation shown in FIG. 2 is obtained.

Alternatively, the two input sides of the inverter 44 could also have a source 14''' connected to them, for example using a current probe, for the time of a test cycle and could have a signal modulated onto them that is produced by an additional periodic load, for example.

As a further option in FIG. 6, the use of an interface 46 of the inverter 44 is shown, which interface could be actuated via a source 14" in order to modulate a suitable signal onto the input circuit of the inverter 44.

A further option for modulation in FIG. 6 is the periodic shading of a portion of the photovoltaic installation or of a photovoltaic module in order to produce excitation, as indicated at 14' in FIG. 1.

Any other options are conceivable.

FIG. 7 schematically shows the current/voltage characteristic of a photovoltaic module. Various operating points indicated are, in particular, short circuit KS, no load LL and operation in the forward direction VR. Owing to the bypass diode, the drop is obtained at the bottom left end after the threshold voltage of >0.5 volt has been overcome. The no load voltage is approximately 36 to 45 volts.

In the short-circuit case, almost all excess charge carriers are sucked away from intact contacts. Therefore, the luminescence signal, which can be read off from the right-hand scale, is almost zero. In the no-load case LL, exclusively photoluminescence PL is obtained, since only excitation by light takes place.

During operation in the forward direction VR, VR=PL+EL, wherein EL>>PL in regions with a good supply of current. Hence, the series resistance definitively determines the difference between VR and LL.

Further down the characteristic, the point of maximum power output is denoted by MPP.

When the photovoltaic module is modulated using the modulation frequency $f_Q$, a periodic alteration is made by changing between at least two operating points. The luminescence signals produced at the various operating points contain different information. Possible operating points are: short circuit (KS), no load (LL), any point in the forward direction (VR) and the maximum power point (MPP).

In the short-circuit case KS, practically all charge carriers are sucked away, which means that the luminescence in the short-circuit case is KL≈0. In the short circuit, the image of a photovoltaic module consequently now consists only of the background radiation H: KS≈H, since KL≈0.

At no load LL, the image of a photovoltaic module consists of the photoluminescence PL and the background H: LL≈PL+H.

In the forward direction VR, the module is connected as a load. The image of a photovoltaic module consists of electroluminescence (EL), photoluminescence (PL) and the background (H). VR≈EL+PL+H is obtained.

When changing between various operating points, the following changes can be detected:

a) The photoluminescence PL is obtained from the difference in the luminescence signals at no load LL and in the short circuit KS: PL=LL−KS.

Information from a photoluminescence image is the no-load voltage of the solar cells included in the photovoltaic module.

It is also possible for uncontacted (dead) regions to be established. The reason is that a change of operating point takes place only in contacted regions: regions in which no changes take place are thus not electrically connected. In addition, it is possible for microfissures and potential-induced degradation (PID) to be established.

b) The difference between the luminescence in the forward direction VR and the luminescence at no load LL produces the current-induced electroluminescence EL=VR−LL.

Information is the local series resistance RS. Regions having high series resistance have less current flow, that is to say that smaller changes are detected.

It is a simple matter to identify regions that have poor electrical connection, such as interrupted fingers, poor solder joints and broken cell connectors. It is also possible for microfissures and potential-induced degradation to be identified.

c) The difference between the luminescence in the forward direction VR and the luminescence in the short circuit KS produces the general luminescence: PL+EL=VR−KS.

This allows assessment of the general quality of the photovoltaic module, particularly the establishment of microfissures and potential-induced degradation with a particularly high SNR.

What is claimed is:

1. A method of testing photovoltaic modules, comprising the steps of:
   modulating a power drawn from or output by or fed into a photovoltaic module using at least one modulation frequency, while operating said photovoltaic module in ambient light and only in a forward direction thereof;
   scanning said photovoltaic module using a camera for outputting a camera signal;
   generating from said camera signal a luminescence image of said photovoltaic module; and
   evaluating said camera signal using a digital filter operating by a lock-in method, while using said camera signal responding to a luminescence output of said photovoltaic module to said modulating step while operating solely under said ambient light.

2. The method of claim 1, further comprising the step of:
   applying a filter system upstream to said camera, said filter system being transmissive in a wavelength range containing luminescence signals from said photovoltaic module.

3. The method of claim 1, wherein said modulation frequency is produced by periodic switching on/off.

4. The method of claim 1, wherein said photovoltaic module is periodically shorted for generating said modulation frequency.

5. The method of claim 1, wherein said photovoltaic module is actuated by periodically modulating irradiation impinging on said photovoltaic module in a portion of said photovoltaic module using said modulation frequency.

6. The method of claim 1, wherein said modulation frequency is generated mechanically, electrically, thermally or magnetically.

7. The method of claim 1, wherein said modulation frequency is in a range from 1 to <25 Hz.

8. A method of testing photovoltaic modules, comprising the steps of:
   modulating a power drawn from or output by or fed into a photovoltaic module using at least one modulation frequency, while operating said photovoltaic module in daylight and only in a forward direction thereof;
   scanning said photovoltaic module using a camera for outputting a camera signal;
   generating from said camera signal a luminescence image of said photovoltaic module;
   evaluating said camera signal using a digital filter operating by a lock-in method;
   wherein said modulation frequency is impressed onto said photovoltaic module, said modulation at said modulation frequency changing periodically between at least two operating points.

9. The method of claim 8, wherein said operating points are selected from the group that consists of short circuit, no load, maximum power point and any point in a forward direction.

10. The method of claim 8, wherein information is extracted from said luminescence signals at different operating points by extracting a difference.

11. The method of claim 8, wherein an ambient light induced photoluminescence PL is extracted by subtracting luminescence signals at no load LL and under short circuit KS: LL−KS=PL.

12. The method of claim 8, wherein a current-induced electroluminescence EL is extracted by subtracting luminescence signals in the forward direction VR and at no load LL: EL=VR−LL.

13. The method of claim 8, wherein an ambient light and current induced general electroluminescence EL+PL is extracted by subtracting luminescence signals in the forward direction VR and under short circuit KS: EL+PL=VR−KS.

14. A method of testing photovoltaic modules, comprising the steps of:
- modulating a power drawn from or output by or fed into a photovoltaic module using at least one modulation frequency, while operating said photovoltaic module in ambient light and only in a forward direction thereof;
- scanning said photovoltaic module using a camera for outputting a camera signal;
- generating from said camera signal a luminescence image of said photovoltaic module;
- evaluating said camera signal using a digital filter operating by a lock-in method and using a response of said photovoltaic module to said modulating step while operating solely under said ambient light;
- wherein said test is performed using a connected load or power source that is connected to said photovoltaic module.

15. The method of claim 14, wherein said connected load or power source is an inverter generating a frequency which is being used as a modulation frequency for MPP search.

16. The method of claim 14, wherein said connected load or power source is an inverter being actuated via an interface using said modulation frequency.

17. A method of testing photovoltaic modules, comprising the steps of:
- modulating a power drawn from or output by or fed into a photovoltaic module using at least one modulation frequency, while operating said photovoltaic module in daylight and only in a forward direction thereof;
- scanning said photovoltaic module using a camera for outputting a camera signal;
- generating from said camera signal a luminescence image of said photovoltaic module;
- evaluating said camera signal using a digital filter operating by a lock-in method;
- wherein said modulating is generated optically by applying supplementary irradiation onto said photovoltaic module leading to additive or subtractive superposition with a primary irradiation impinging onto said photovoltaic module.

18. A method of testing photovoltaic modules, comprising the steps of:
- modulating a power drawn from or output by or fed into a photovoltaic module using at least one modulation frequency, while operating said photovoltaic module in ambient light and in a forward direction thereof;
- scanning said photovoltaic module using a camera for outputting a camera signal; and
- evaluating said camera signal using an algorithm for generating from said camera signal an electroluminescence image of said photovoltaic module, using a luminescence response of said photovoltaic module to said modulating step while operating solely under said ambient light.

19. The method of claim 18, wherein said luminescence image is evaluated for detecting defects on said photovoltaic module.

20. An apparatus for testing a photovoltaic module while being operated in forward direction, said apparatus comprising:
- a modulator for modulating an AC voltage signal onto the power drawn or output by or fed into said photovoltaic module using at least one modulation frequency, said modulating at said modulation frequency changing periodically between at least two operating points;
- a camera arranged for scanning said photovoltaic module, said camera outputting a camera signal;
- an evaluation device comprising an algorithm for computing a luminescence image from said camera signal and for detecting defects on said photovoltaic module.

* * * * *